(12) United States Patent
Chen et al.

(10) Patent No.: US 8,329,410 B2
(45) Date of Patent: Dec. 11, 2012

(54) METHOD FOR DIAGNOSING KIDNEY DISEASE COMPRISING DETECTING THE LEVEL OF ANNEXIN A2

(75) Inventors: Ann Chen, Taipei (TW); Shuk-Man Ka, Taipei (TW); Chao-Wen Cheng, Magong (TW); Jenn-Han Chen, Taipei (TW); Chen-Wen Yao, Taipei (TW)

(73) Assignee: National Defense Medical Center, Taipei (TW)

( * ) Notice: Subject to any disclaimer, the term of this patent is extended or adjusted under 35 U.S.C. 154(b) by 297 days.

(21) Appl. No.: 12/540,146

(22) Filed: Aug. 12, 2009

(65) Prior Publication Data

US 2010/0081142 A1 Apr. 1, 2010

Related U.S. Application Data

(62) Division of application No. 11/407,101, filed on Apr. 20, 2006, now abandoned.

(30) Foreign Application Priority Data

Jan. 2, 2006 (TW) ................................ 95100063 A

(51) Int. Cl.
*G01N 33/53* (2006.01)
*C12Q 1/68* (2006.01)
*C07K 14/47* (2006.01)
(52) U.S. Cl. ........... 435/7.1; 435/6.1; 530/350; 530/835
(58) Field of Classification Search ........................ None
See application file for complete search history.

(56) References Cited

U.S. PATENT DOCUMENTS

| 5,541,308 | A | 7/1996 | Hogan |
| 6,582,908 | B2 | 6/2003 | Fodor |
| 2002/0110832 | A1 | 8/2002 | Pyle |
| 2003/0157573 | A1 * | 8/2003 | Mor ................................ 435/7.2 |
| 2003/0232334 | A1 | 12/2003 | Morris |

OTHER PUBLICATIONS

Cheng et al #1, Dec. 2005. Kidney International. 68: 2694-2703.*
Cheng et al #2, Jun. 2005. Nephrology (Carlton). 10 Suppl 1: A4.*
"Acute Renal Failure" by James McMillan, Dec. 2007, Merck Manual, on-line at www.merckmanuals.com, 9 pages as printed.*
"Acute Tubular Necrosis" by Navin Jaipul, Aug. 2009, Merck Manual, on-line at www.merckmanuals.com, 4 pages as printed.*
Dreier et al, 1998 (Histochem Cell Biol. 110: 137-148).*
Zimmerman et al, 2004. Virchows Arch. 445: 368-374.*
Ka et al, 2006. Nephrol Dial Transplant. 21: 288-298.*
Hayes et al, 2004. Sub-Cellular Biochemistry. 45:1-28.*
Farnsworth, et al , Biology of Reproduction 1998 vol. 59 p. 546.
GenBank Accession No. BC003832 (Feb. 13, 2004).
GenBank Accession No. Ay400688 (Dec. 15, 2003).
GenBank Accession No. A7400686 (NCBI Website Dec. 13, 2003).
Hirschhorn et al (Genetics in Medicine. vol. 4, No. 2, pp. 45-61, Mar. 2002).

* cited by examiner

*Primary Examiner* — Zachary Howard
(74) *Attorney, Agent, or Firm* — Ditthavong Mori & Steiner, P.C.

(57) ABSTRACT

The present invention provides biomarkers for detecting kidney disease, selected from the oligonucleotide sequence, complementary sequence or derivatives, amino acid sequence or derivatives, fragment, variants, antibody of annexin A2 or S100A6 or combinations thereof. Moreover, the present invention also provides an assay kit and a method for kidney disease detecting, practically for the kidney disease resulting from acute tubular necrosis.

9 Claims, 9 Drawing Sheets

SEQUENCE LISTING

<160> NUMBER OF SEQ ID NOS: 12

<210> SEQ ID NO 1
<211> LENGTH: 1020
<212> TYPE: DNA
<213> ORGANISM: human Annexin A2 cDNA

<400> SEQUENCE: 1

```
atgtctactg ttcacgaaat cctgtgcaag ctcagcttgg agggtgatca ctctacaccc      60
ccaagtgcat atgggtctgt caaagcctat actaactttg atgctgagcg ggatgctttg     120
aacattgaaa cagccatcaa gaccaaaggt gtggatgagg tcaccattgt caacattttg     180
accaaccgca gcaatgcaca gagacaggat attgccttcg cctaccagag aaggaccaaa     240
aaggaacttg catcagcact gaagtcagcc ttatctggcc acctggagac ggtgattttg     300
ggcctattga agacacctgc tcagtatgac gcttctgagc taaaagcttc catgaagggg     360
ctgggaaccg acgaggactc tctcattgag atcatctgct ccagaaccaa ccaggagctg     420
caggaaatta cagagtctca aggaaatg tacaagactg atctggagaa ggacattatt     480
tcggacacat ctggtgactt ccgcaagctg atggttgccc tggcaaaggg tagaagagca     540
gaggatggct ctgtcattga ttatgaactg attgaccaag atgctcggga tctctatgac     600
gctggagtga agaggaaagg aactgatgtt cccaagtgga tcagcatcat gaccgagcgg     660
agcgtgcccc acctccagaa agtatttgat aggtacaaga gttacagccc ttatgacatg     720
ttggaaagca tcaggaaaga ggttaaagga gacctggaaa atgctttcct gaacctggtt     780
cagtgcattc agaacaagcc cctgtatttt gctgatcggc tgtatgactc catgaagggc     840
aaggggacgc gagataaggt cctgatcaga atcatggtct cccgcagtga agtggacatg     900
ttgaaaatta ggtctgaatt caagagaaag tacggcaagt ccctgtacta ttatatccag     960
caagacacta gggcgactac cagaaagcg ctgctgtacc tgtgtggtgg agatgactga    1020
```

<210> SEQ ID NO 2
<211> LENGTH: 339
<212> TYPE: PRT
<213> ORGANISM: human Annexin A2 protein

<400> SEQUENCE: 2

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

```
Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
    290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 3
<211> LENGTH: 273
<212> TYPE: DNA
<213> ORGANISM: human Calcyclin S100A6 cDNA

<400> SEQUENCE: 3
atggcatgcc cctggatca ggccattggc ctcctcgtgg ccatcttcca caagtactcc      60
ggcagggagg gtgacaagca caccctgagc aagaaggagc tgaaggagct gatccagaag    120
gagctcacca ttggctcgaa gctgcaggat gctgaaattg caaggctgat ggaagacttg    180
gaccggaaca aggaccagga ggtgaacttc caggagtatg tcaccttcct gggggccttg    240
gctttgatct acaatgaagc cctcaagggc tga                                 273

<210> SEQ ID NO 4
<211> LENGTH: 90
<212> TYPE: PRT
<213> ORGANISM: human Calcyclin S100A6 protein

<400> SEQUENCE: 4

Met Ala Cys Pro Leu Asp Gln Ala Ile Gly Leu Leu Val Ala Ile Phe
1               5                   10                  15

His Lys Tyr Ser Gly Arg Glu Gly Asp Lys His Thr Leu Ser Lys Lys
                20                  25                  30

Glu Leu Lys Glu Leu Ile Gln Lys Glu Leu Thr Ile Gly Ser Lys Leu
            35                  40                  45

Gln Asp Ala Glu Ile Ala Arg Leu Met Glu Asp Leu Asp Arg Asn Lys
        50                  55                  60

Asp Gln Glu Val Asn Phe Gln Glu Tyr Val Thr Phe Leu Gly Ala Leu
65                  70                  75                  80
```

Ala Leu Ile Tyr Asn Glu Ala Leu Lys Gly
            85                  90

```
<210> SEQ ID NO 5
<211> LENGTH: 21
<212> TYPE: DNA
<213> ORGANISM: artificial sequence
<220> FEATURE:
<223> OTHER INFORMATION: chemically synthesized

<400> SEQUENCE: 5
cgcttcttct agcccagtca t                                           21

<210> SEQ ID NO 6
<211> LENGTH: 21
<212> TYPE: DNA
<213> ORGANISM: artificial sequence
<220> FEATURE:
<223> OTHER INFORMATION: chemically synthesized

<400> SEQUENCE: 6
actggatttc accgagagag g                                           21

<210> SEQ ID NO 7
<211> LENGTH: 2039
<212> TYPE: DNA
<213> ORGANISM: artificial sequence
<220> FEATURE:
<223> OTHER INFORMATION: chemically synthesized

<400> SEQUENCE: 7
gatcagcgaa acacttttaa tcatctccgc cgctgggttt cacccgccg ccattttttg    60 ctgcatcagc acgaaattct taaagccctg gttacgtacc agtgacatac cgataactga   120
cgtgaatata accagcacga gggtcagcaa tacccccaat acatgggcaa cctgaataaa   180
gattgaaatc tcaatataga cataaaggaa aatggcaata aaaggtaacc agcgcaaagg   240
tttctcctgt aatagcagcc ggttaacccc ggctacctga atgggttgcg aatcgcgttt   300
agcttatatt gtggtcatta gcaaaatttc aagatgtttg cgcaactatt tttggtagta   360
atcccaaagc ggtgatctat ttcacaaatt aataattaag gggtaaaaac cgacacttaa   420
agtgatccag attacggtag aaatcctcaa gcagcatatg atctcgggta ttcggtcgat   480 gcagggggata atcgtcggtc gaaaaacatt cgaaaccaca tatattctgt gtgtttaaag   540
caaatcattg gcagcttgaa aaagaaggtt cacatgtcaa acaacattcg tatcgaagaa   600
gatctgttgg gtaccaggga agttccagct gatgcctact atggtgttca cactctgaga   660
gcgattgtaa acttctatat cagcaacaac aaaatcagtg atattcctga atttgttcgc   720
ggtatggtaa tggttaaaaa agccgcagct atggcaaaca aagagctgca aaccattcct   780
aaaagtgtag cgaatgccat cattgccgca tgtgatgaag tcctgaacaa cggaaaatgc   840
atggatcagt tcccggtaga cgtctaccag ggcggcgcag gtacttccgt aaacatgaac   900
accaacgaag tgctggccaa tatcggtctg aactgatgg gtcaccaaaa aggtgaatat   960
cagtacctga acccgaacga ccatgttaac aaatgtcagt ccactaacga cgcctacccg  1020
accggtttcc gtatcgcagt ttactcttcc ctgattaagc tggtagatgc gattaaccaa  1080
ctgcgtgaag ctttgaacg taaagctgtc gaattccagg acatcctgaa atgggtcgt   1140 acccagctgc aggacgcagt accgatgacc ctcggtcagg aattccgcgc tttcagcatc  1200
ctgctgaaaa agaagtgaa aaacatccaa cgtaccgctg aactgctgct ggaagttaac  1260
cttggtgcaa cagcaatcgg tactggtctg aacacgccga aagagtactc tccgctggca  1320
```

```
gtgaaaaaac tggctgaagt tactggcttc ccatgcgtac cggctgaaga cctgatcgaa      1380
gcgacctctg actgcggcgc ttatgttatg gttcacggcg cgctgaaacg cctggctgtg      1440
aagatgtcca aaatctgtaa cgacctgcgc ttgctctctt caggcccacg tgccggcctg      1500
aacgagatca acctgccgga actgcaggcg ggctcttcca tcatgccagc taaagtaaac      1560
ccggttgttc cggaagtggt taaccaggta tgcttcaaag tcatcggtaa cgacaccact      1620
gttaccatgg cagcagaagc aggtcagctg cagttgaacg ttatggagcc ggtcattggc      1680
caggccatgt tcgaatccgt tcacattctg accaacgctt gctacaacct gctggaaaaa      1740
tgcattaacg gcatcactgc taacaaagaa gtgtgcgaag gttacgttta caactctatc      1800
ggtatcgtta cttacctgaa cccgttcatc ggtcaccaca acggtgacat cgtgggtaaa      1860
atctgtgccg aaaccggtaa gagtgtacgt gaagtcgttc tggaacgcgg tctgttgact      1920
gaagcggaac ttgacgatat tttctccgta cagaatctga tgcacccggc ttacaaagca      1980
aaacgctata ctgatgaaag cgaacagtaa tcgtacaggg tagtacaaat aaaaaaggc      2039

<210> SEQ ID NO 8
<211> LENGTH: 21
<212> TYPE: DNA
<213> ORGANISM: artificial sequence
<220> FEATURE:
<223> OTHER INFORMATION: chemically synthesized

<400> SEQUENCE: 8
gtcggttcct ttcctcttca c                                                 21

<210> SEQ ID NO 9
<211> LENGTH: 270
<212> TYPE: DNA
<213> ORGANISM: mouse Calcyclin S100A6 cDNA

<400> SEQUENCE: 9
atggcatgcc ctctggatca ggccattggc cttctcgtgg ccatcttcca caagtactct        60
ggcaaggaag gtgacaagca caccctgagc aagaaggagc tgaaggagtt gatccagaag       120
gagctcacca ttggctccaa gctgcaggat gctgaaattg caaggctgat ggatgatctg       180
gaccgtaaca aggatcagga agtaaacttc caggagtatg tcgccttcct gggggccttg       240
gctttgatct acaatgaagc tctgaaataa                                         270

<210> SEQ ID NO 10
<211> LENGTH: 89
<212> TYPE: PRT
<213> ORGANISM: mouse Calcyclin S100A6 protein

<400> SEQUENCE: 10

Met Ala Cys Pro Leu Asp Gln Ala Ile Gly Leu Leu Val Ala Ile Phe
1               5                   10                  15

His Lys Tyr Ser Gly Lys Glu Gly Asp Lys His Thr Leu Ser Lys Lys
            20                  25                  30

Glu Leu Lys Glu Leu Ile Gln Lys Glu Leu Thr Ile Gly Ser Lys Leu
        35                  40                  45

Gln Asp Ala Glu Ile Ala Arg Leu Met Asp Asp Leu Asp Arg Asn Lys
    50                  55                  60

Asp Gln Glu Val Asn Phe Gln Glu Tyr Val Ala Phe Leu Gly Ala Leu
65                  70                  75                  80

Ala Leu Ile Tyr Asn Glu Ala Leu Lys
                85
```

<210> SEQ ID NO 11
<211> LENGTH: 1020
<212> TYPE: DNA
<213> ORGANISM: mouse Annexin A2 cDNA

<400> SEQUENCE: 11

```
atgtctactg tccacgaaat cctgtgcaag ctcagcctgg agggtgatca ttctacaccc      60
ccaagtgcct acgggtcagt caaaccctac accaacttcg atgctgagag ggatgctctg     120
aacattgaga cagcagtcaa gaccaaagga gtggatgagg tcaccattgt caacatcctg     180
acaaaccgca gcaatgtgca gaggcaggac attgccttcg cctatcagag aaggaccaaa     240
aaggagctcc cgtcagcgct gaagtcagcc ttatctggcc acctggagac ggtgattttg     300
ggcctattga agacacctgc ccagtatgat gcttcggaac taaaagcttc catgaagggc     360
ctggggactg acgaggactc cctcattgag atcatctgct cccgaaccaa ccaggagctg     420
caagagatca cagagtgtat caaggaaatg tacaagactg atctggagaa ggacatcatc     480
tctgacacat ctggagactt ccgaaagctg atggtcgccc ttgcaaaggg cagacgagca     540
gaggatggct cagttattga ctacgagctg attgaccagg atgcccggga gctctatgat     600
gccggggtga agaggaaagg aaccgacgtc cccaagtgga tcagcatcat gactgagcgc     660
agtgtgtgcc acctccagaa agtgttcgaa aggtacaaga gctacagccc ttatgacatg     720
ctggagagca tcaagaaaga ggtcaaaggg gacctggaga cgccttcct gaacctggtc      780
cagtgcatcc agaacaagcc cctgtacttc gctgaccggc tgtacgactc catgaagggc     840
aaggggactc gagacaaggt cctgattaga atcatggtct ctcgcagtga agtggacatg     900
ctgaaaatca gatctgaatt caagaggaaa tatggcaagt ccctgtacta ctacatccag     960
caagacacca agggtgacta ccagaaggca ctgctgtacc tgtgtggtgg ggatgactga    1020
```

<210> SEQ ID NO 12
<211> LENGTH: 339
<212> TYPE: PRT
<213> ORGANISM: mouse Annexin A2 protein

<400> SEQUENCE: 12

```
Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Pro Tyr Thr Asn
            20                  25                  30

Phe Asp Ala Glu Arg Asp Ala Leu Asn Ile Glu Thr Ala Val Lys Thr
        35                  40                  45

Lys Gly Val Asp Glu Val Thr Ile Val Asn Ile Leu Thr Asn Arg Ser
    50                  55                  60

Asn Val Gln Arg Gln Asp Ile Ala Phe Ala Tyr Gln Arg Arg Thr Lys
65                  70                  75                  80

Lys Glu Leu Pro Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160
```

```
Ser Asp Thr Ser Gly Asp Phe Arg Lys Leu Met Val Ala Leu Ala Lys
            165                 170                 175

Gly Arg Arg Ala Glu Asp Gly Ser Val Ile Asp Tyr Glu Leu Ile Asp
            180                 185                 190

Gln Asp Ala Arg Glu Leu Tyr Asp Ala Gly Val Lys Arg Lys Gly Thr
        195                 200                 205

Asp Val Pro Lys Trp Ile Ser Ile Met Thr Glu Arg Ser Val Cys His
        210                 215                 220

Leu Gln Lys Val Phe Glu Arg Tyr Lys Ser Tyr Ser Pro Tyr Asp Met
225                 230                 235                 240

Leu Glu Ser Ile Lys Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
        290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
            325                 330                 335

Gly Asp Asp
```

METHOD FOR DIAGNOSING KIDNEY DISEASE COMPRISING DETECTING THE LEVEL OF ANNEXIN A2

CROSS-REFERENCES TO RELATED APPLICATIONS

This application is a divisional of U.S. application Ser. No. 11/407,101 filed on Apr. 20, 2006, now abandoned, and clams the benefit of Taiwan Patent Application No. 095100063 filed Jan. 6, 2006.

BACKGROUND OF THE INVENTION

1. Field of the Invention

The present invention is related to an innovative method to select acute tubular necrosis-related acute renal failure patient by detecting protein or nucleotide of annexin A2 and/or S100A6.

2. Description of the Prior Art

Acute tubular necrosis (ATN) is the most common pathologic entity responsible for the clinical state of acute renal failure (ARF) [1, 2]. The two main causes of ATN are ischemic and toxic injuries [3]. In the latter type, a variety of renal environmental substances that include heavy metals such as mercury, lead, and uranium are known to cause ARF. Nephrotoxic ATN is histologically evident as epithelial cell necrosis, mainly in the proximal convoluted tubules, with preservation of the tubular basement membrane, and usually intact distal tubular segments [4].

Although severely damaged by toxin, the kidney has the ability to completely recover structurally and functionally. Normally, quiescent cells undergo dedifferentiation and regain their potential to divide after enhancement of DNA synthesis in ATN. Consequent to cell proliferation, the new cells differentiate to restore the functional integrity of the nephron [5]. Little is known of the mechanism (s) by which regeneration of renal tubules is mediated. The observations that hepatocyte growth factor, epidermal growth factor, and bone morphogenetic protein-7 are among the potent regulators of kidney organogenesis, and that these agents can also promote tubular regeneration after a variety of insults [6], are consistent with the idea that the regeneration process may be partially controlled by a mechanism similar to that operating during development. Tubular cell calcium concentration and content are increased following acute renal injury induced by ischemic and toxic insults. The divalent calcium cation ($Ca^{2+}$)-signaling system operate by binding to effector molecules, $Ca^{2+}$-binding proteins, that mediate stimulation of numerous Ca2+-dependent processes such as transcription and cell proliferation. Two large families of the Ca2+-binding proteins are the annexins and the EF-hand motif S100 proteins [7]. The annexins are a family of 5 phospholipids binding proteins that share a common property of interacting with membranes and target molecules in a Ca2+-dependent manner [8, 9]. S100 proteins represent the largest subgroup in the EF-hand $Ca^{2+}$-binding protein family. A unique feature of S100 proteins is that individual members are localized in specific cellular compartments from which some are able to relocate upon Ca2+ activation, thus transducing the $Ca^{2+}$ signal in a temporal and spatial manner by interacting with different targets specific for each S100 protein [10]. Interactions between annexins and S100 proteins are now known to include several members of these protein families.

Therefore, it's helpful to search useful biomarkers in annexins and S100 protein groups for detecting the reason of acute kidney failure in clinical medical diagnosis.

SUMMARY OF THE INVENTION

To address the problem of detecting acute kidney failure, the present invention provides a biomarker for detecting kidney disease, selected from the oligonucleotide sequence, complementary sequence or derivatives, amino acid sequence or derivatives, fragment, variants, antibody of annexin A2 or S100A6 or combinations thereof.

Another object of the present invention is to provide a biomarker for detecting kidney disease, selected from the oligonucleotide sequence, complementary sequence or derivatives of SEQ ID NO: 1, SEQ ID NO: 11, SEQ ID NO: 3 or SEQ ID NO: 9, amino acid sequence or derivatives, fragment, variants, antibody of SEQ ID NO: 2, SEQ ID NO: 12, SEQ ID NO: 4 or SEQ ID NO: 10 or combinations thereof.

Yet another object of the present invention is to provide an assay kit for kidney disease, comprising biomarkers. The biomarkers are selected from the oligonucleotide sequence, complementary sequence or derivatives, amino acid sequence or derivatives, fragment, variants, antibody of annexin A2 or S100A6 or combinations thereof.

Another object of the present invention is to provide a diagnosis method for kidney disease, comprising the following steps: (a) providing a sample; (b) providing biomarkers which are selected from: oligonucleotide sequence, complementary sequence or derivatives of SEQ ID NO: 1, SEQ ID NO: 11, SEQ ID NO: 3 or SEQ ID NO: 9, amino acid sequence or derivatives, fragments, variants, antibody of SEQ ID NO: 2, SEQ ID NO: 12, SEQ ID NO: 4 or SEQ ID NO: 10, or combinations thereof; (c) contacting said biomarkers in step (b) with the substance of the sample in step (a), the substance is selected from the oligonucleotide sequence, complementary sequence or derivatives, amino acid sequence or derivatives, fragment, variants, antibody of annexin A2 or S100A6 or combinations thereof; (d) detecting the products of the biomarkers reacting with the substance in step (c).

BRIEF DESCRIPTION OF THE DRAWINGS

FIG. 2a, normal kidney cells (day 0); FIG. 2b, day 3 after induction; FIG. 2c, day 7 after induction; and FIG. 2d, day 14 after induction.

FIG. 4a, expression of S100A6 of control animal (day 0); FIG. 4b, expression of annexin A2 of control animal (day 0); FIG. 4c, expression of S100A6 at day 3; FIG. 4d, expression of annexin A2 at day 3; FIG. 4e, expression of S100A6 at day 7; FIG. 4f, expression of annexin A2 at day 7; FIG. 4g, expression of S100A6 at day 14; and FIG. 4h, expression of annexin A2 at day 14.

FIG. 5a, expression of S100A6; FIG. 5b, expression of annexin A2; FIG. 5c, results of semi-quantitative scoring analysis; and FIG. 5d, results of S100A6 and annexin A2 double staining FIG. 6a, temporal pattern of S100A6 expression in folic acid ATN model; FIG. 6b, temporal pattern of S100A6 expression in IRI ARF model; FIG. 6c, temporal pattern of annexin A2 expression in folic acid ATN model; and FIG. 6d, temporal pattern of annexin A2 expression in IRI ARF model.

DETAILED DESCRIPTION OF THE INVENTION

Figure 1:
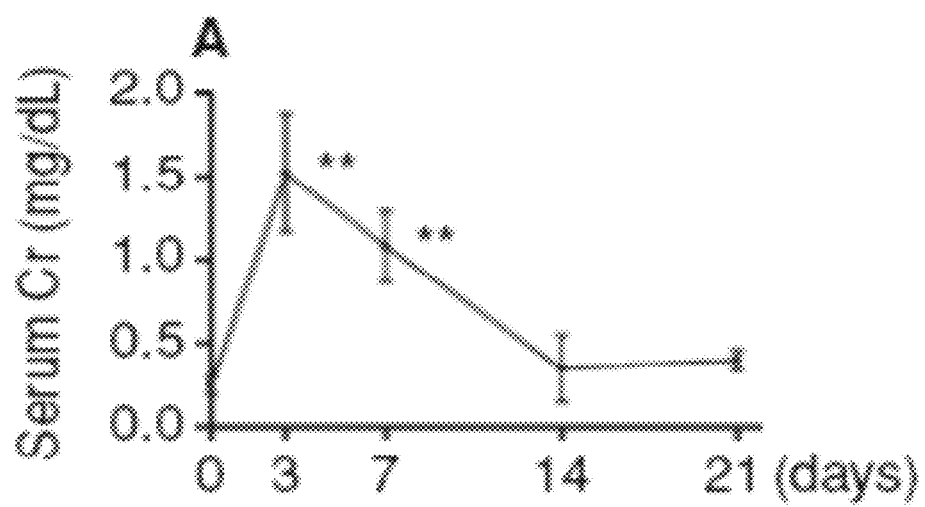
FIG. 1a shows the value of serum creatinine in uranyl-nitrate induced ATN animal model of the example 1.
FIG. 1b shows the value of serum BUN in uranyl-nitrate induced ATN animal model of the example 1.
FIG. 1c shows day 0 of renal tissue sections in uranyl-nitrate induced ATN animal model of the example 1.
FIG. 1d shows day 3 of renal tissue sections in uranyl-nitrate induced ATN animal model of the example 1.
FIG. 1e shows day 7 of renal tissue sections in uranyl-nitrate induced ATN animal model of the example 1.
FIG. 1f shows day 14 of renal tissue sections in uranyl-nitrate induced ATN animal model of the example 1.
FIG. 1g shows polygon of renal necrosis score in uranyl-nitrate induced ATN animal model of the example 1.
FIG. 1h shows polygon of renal regeneration score in uranyl-nitrate induced ATN animal model of the example 1.
Figure 1:
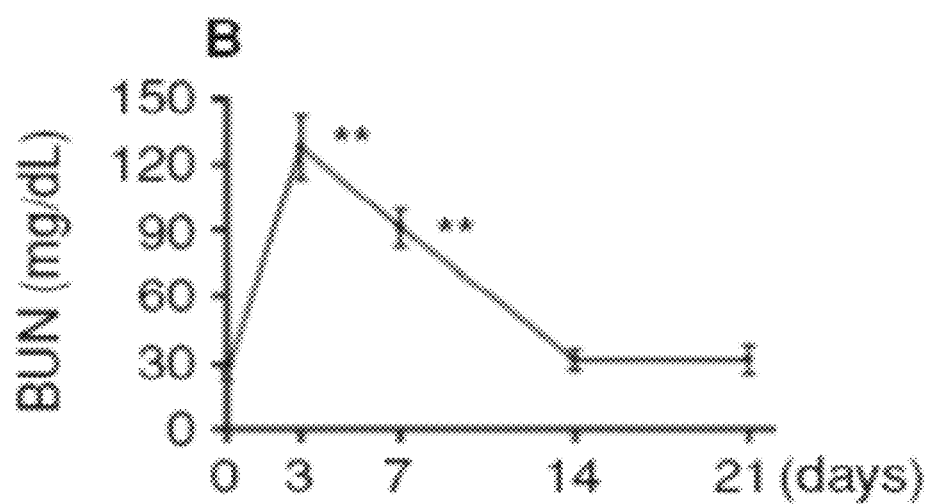
Figure 1:
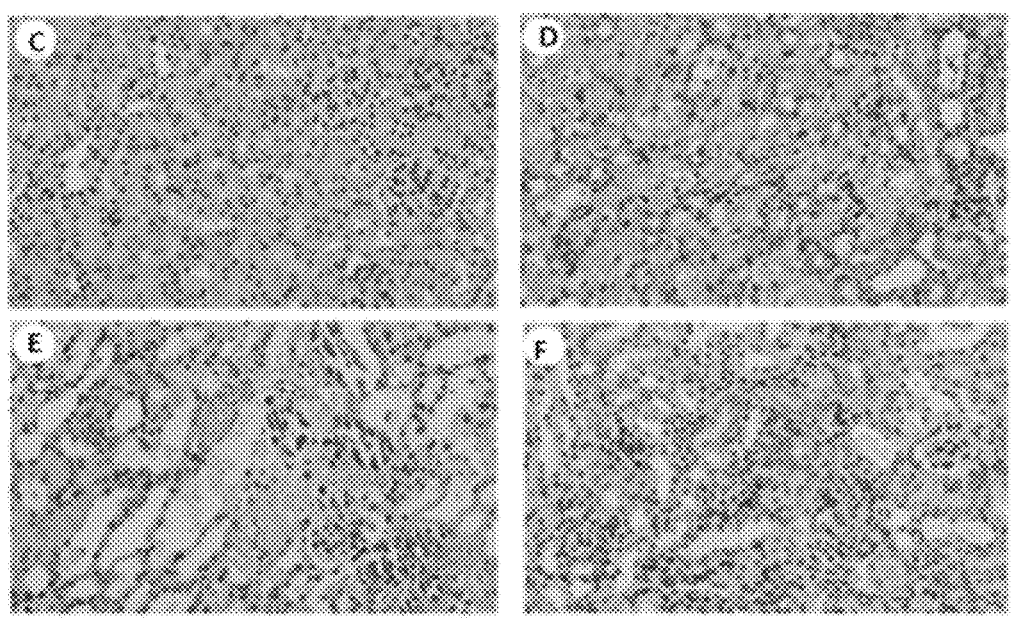
Figure 1:
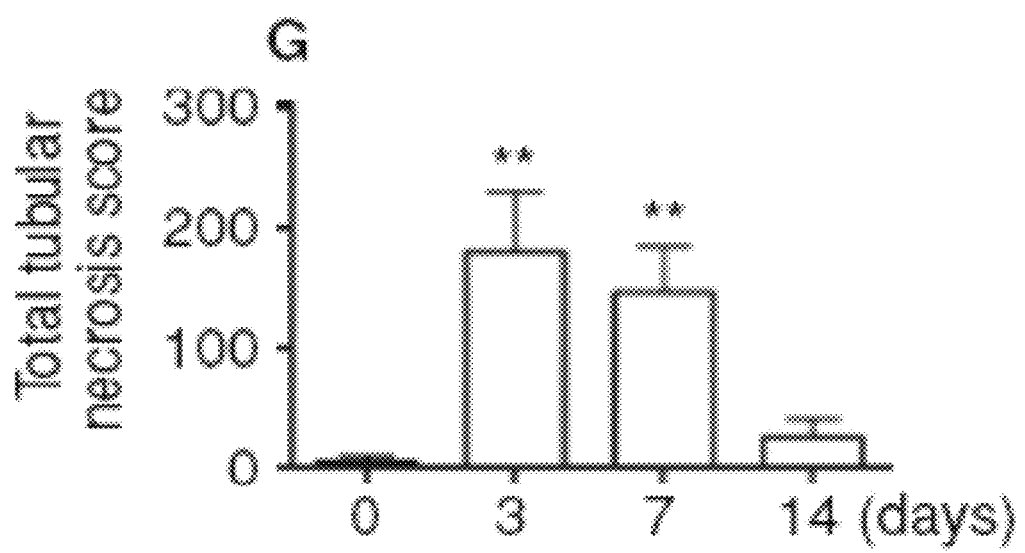
Figure 1:
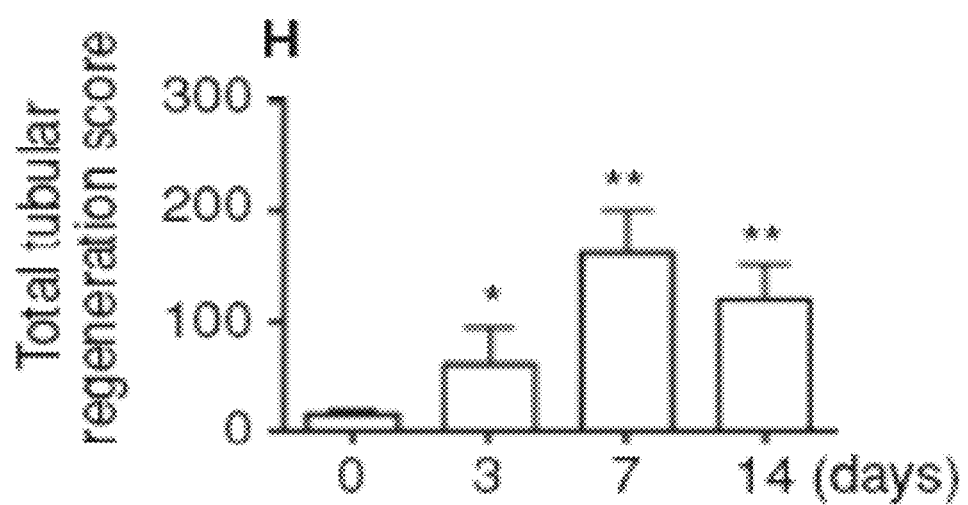

One of the objects in the present invention is to provide a biomarker for detecting kidney disease, selected from the oligonucleotide sequence, complementary sequence or derivatives, amino acid sequence or derivatives, fragment, variants, antibody or combination of annexin A2 or S100A6. The kidney disease is acute renal failure, specifically, resulting from acute tubular necrosis.

Aforesaid oligonucleotide sequence of annexin A2 is selected from SEQ ID NO: 1 or SEQ ID NO: 11.

Aforesaid amino acid sequence of annexin A2 is selected from SEQ ID NO: 2 or SEQ ID NO: 12.

Aforesaid oligonucleotide sequence of S100A6 is selected from SEQ ID NO: 3 or SEQ ID NO: 9.

Aforesaid amino acid sequence of S100A6 is selected from SEQ ID NO: 4 or SEQ ID NO: 10.

Aforesaid variants of annexin A2 or S100A6 have 80% or more than 80% similarity with the amino acid sequence of annexin A2 or S100A6.

Aforesaid derivatives are to modify the 3' terminal or 5'terminal of said oligonucleotide sequence or complementary sequence and keeping 70% or more than 70% similarity with the oligonucleotide sequence of annexin A2 or S100A6. Selectively, the similarity is keeping 90% or more than 90%.

Another object of the present invention is to provide a biomarker for detecting kidney disease, selected from the oligonucleotide sequence, complementary sequence or derivatives of SEQ ID NO: 1, SEQ ID NO: 11, SEQ ID NO: 3 or SEQ ID NO: 9, amino acid sequence or derivatives, fragment, variants, antibody of SEQ ID NO: 2, SEQ ID NO: 12, SEQ ID NO: 4 or SEQ ID NO: 10 or combinations thereof. The kidney disease is acute renal failure, specifically, resulting from acute tubular necrosis.

Aforesaid variants have 80% or more than 80% similarity with the amino acid sequence of SEQ ID NO: 2, SEQ ID NO: 12, SEQ ID NO: 4 or SEQ ID NO: 10.

Aforesaid derivatives of SEQ ID NO: 1, SEQ ID NO: 11, SEQ ID NO: 3 or SEQ ID NO: 9 are to modify the 3' terminal or 5'terminal of said oligonucleotide sequence or complementary sequence and keeping 70% or more than 70% similarity with the oligonucleotide sequence.

Aforesaid derivatives of SEQ ID NO: 1, SEQ ID NO: 11, SEQ ID NO: 3 or SEQ ID NO: 9 are to modify the 3' terminal or 5'terminal of said oligonucleotide sequence or complementary sequence and keeping 90% or more than 90% similarity with the oligonucleotide sequence.

Yet another object of the present invention is to provide an assay kit for kidney disease, including one or more biomarkers. The biomarkers can be selected from oligonucleotide sequence, complementary sequence or derivatives, amino acid sequence or derivatives, fragment, variants, antibody of annexin A2 or S100A6. The preceding candidates of annexin A2 or S100A6 can be selected in any combination at will. The kidney disease is acute renal failure, specifically, resulting from acute tubular necrosis.

Aforesaid oligonucleotide sequence of annexin A2 is selected from SEQ ID NO: 1 or SEQ ID NO: 11.

Aforesaid amino acid sequence of annexin A2 is selected from SEQ ID NO: 2 or SEQ ID NO: 12.

Aforesaid oligonucleotide sequence of S100A6 is selected from SEQ ID NO: 3 or SEQ ID NO: 9.

Aforesaid amino acid sequence of S100A6 is selected from SEQ ID NO: 4 or SEQ ID NO: 10.

The kit can comprise secondary antibodies of any amino acid sequence or derivatives, fragment, variants, antibody of annexin A2 or S100A6 or combinations thereof.

Another object of the present invention is to provide a diagnosis method for kidney disease. First, a sample is supplies. Then, biomarkers are provided, which are selected from: the oligonucleotide sequence, complementary sequence or derivatives, amino acid sequence or derivatives, fragment, variants, antibody of annexin A2 or S100A6 or combinations thereof. The biomarkers then are contacted with the substance of the sample, selecting from the oligonucleotide sequence, complementary sequence or derivatives, amino acid sequence or derivatives, fragment, variants, antibody of annexin A2 or S100A6 or combinations thereof. Finally, the product of the biomarkers reacting with the substance is detected by biotechnology. Note should be added that the biotechnology can be, for example, but not limit to, enzyme-linked immunosorbent assay (ELISA), radioimmunoassay (RIA), immunofluorescence, reverse-transcription polymerase chain reaction (RT-PCR) or in situ hybridization. Furthermore, the biomarkers can be fixed on substrate before contacted with the sample. The substrate is ELISA plate or bio-chips.

According to the method of the present invention, one more steps of recognizing antibody with secondary antibody can be added before detecting the product of the biomarkers reacting with the substance.

Preferably, the substance in the sample can be further labelled by fluorescence prior to contacting with biomarkers.

Aforesaid kidney disease is acute renal failure, specifically, resulting from acute tubular necrosis.

The present invention opens the possibilities of utilizing oligonucleotide sequence or amino acid sequence of annexin A2 and/or S100A6 as biomarkers for detecting the type of acute renal failure (especially acute tubular necrosis) and proceeding clinical diagnosis and treatment.

The advantages of the present invention are further depicted with the illustration of examples. The following is a description of the exemplary case of carrying out the platelets provided by the invention for bioactivity testing. This exemplary case is not to be taken in a limiting sense, but is made merely for the purpose of further illustrating the materials and methods for practicing the present invention.

EXAMPLES

Animal Models

Urany-nitrate induced ATN. Female 8-week-old C57BL/6 mice were purchased from the National Laboratory Animal Breeding and Research Center (Taipei, Taiwan). All mice received a single tail vein injection of uranyl nitrate ((UO2 (NO3)2).6H20; 100 µg in 100 µL of 5% NaHCO3). The mice were sacrificed at 0, 3, 7 and 14 days after the injection. Blood and urine were collected for clinical evaluation, and kidneys were removed for molecular and histopathology studies. Samples intended for histopathology were fixed in formalin according to a standard protocol.

Ischemic reperfusion injury. This model was induced as previously described [11]. Briefly, bilateral ischemic reperfusion injury was generated in female Balb/c mice (25-30 g) by occluding the renal pedicles with microvascular clamps for 30 min under ketamine-xylazine anesthesia. Completeness of ischemia was verified by blanching of the kidneys, signifying the stoppage of blood flow. The blood flow to the kidneys was reestablished by removal of the clamps (reperfusion) with visual verification of blood return. Mice subjected to sham operation (identical treatment except that the renal pedicles were not clamped) were used as controls. During the procedure, animals were well hydrated and their body temperature maintained with an adjustable heating pad. At 4, 12, 24, and 72 hours post-ischemia, mice were killed, and their kidneys were removed for RNA extraction.

Folic acid induced acute renal failure. Folic acid (240 mg/kg) was administered into female Balb/c mice (25-30 g) in vehicle (0.2 ml of 0.3MNaHCO3) or vehicle only by intraperitoneal injection [12]. The control kidneys were analyzed before folic acid or vehicle administration. The mice were sacrificed, and their kidneys were collected at 1, 3, 7, and 14 days at each time point.

Renal Function

Blood samples collected through the retro-orbital venous plexus were centrifuged (3000×g, 10 min), and the supernatant containing the serum was withdrawn and stored at −70° C. until assayed. Renal function was assessed by measuring the elevation in plasma levels of creatinine and blood urea nitrogen (BUN). These analyses, which utilized Fuji DRI-CHEM 3030 (Fuji Photo Film Co. Ltd., Tokyo, Japan), were obtained within 15 min once the serum samples thawed.

Renal Histopathology

The formalin-fixed renal tissues were dehydrated in a graded series of ethanol solutions and embedded in paraffin as described elsewhere [13]. Three-micron sections were obtained and stained with H&E. For typical lesions of ATN, tubular cell necrosis, of which some of them were sloughed into the tubular lumina accompanied by casts [14].

Quantitative analysis of renal tubular necrosis was performed by optical microscopy. Briefly, 100 intersections were examined for each kidney and a score from 0 to 3 was given for each tubular profile involving an intersection: 0, normal histology; 1, tubular cell swelling, brush border loss, nuclear condensation, with up to one third of tubular profile showing nuclear loss; 2, as for score 1, but greater than one third and less than two thirds of tubular profile shows nuclear loss; and 3, greater than two thirds of tubular profile shows nuclear loss. The total score for each kidney was is calculated by addition of all 100 scores with a maximum score of 300. There was also evidence of tubular cell regeneration, it was defined as flattened epithelial cells with hyperchromatic nuclei and mitotic figures [14]. Quantitative analysis of renal tubular regeneration was performed by optical microscopy. Briefly, 100 intersections were examined for each kidney and a score from 0 to 3 was given for each tubular profile involving an intersection: 0, normal histology; 1, flattened epithelial cells with hyperchromatic nuclei and mitotic figures with up to one third of tubular profile showing hyperchromatic nuclei and mitotic figures; 2, as for score 1, but greater than one third and less than two thirds of tubular profile shows hyperchromatic nuclei and mitotic figures; and 3, greater than two thirds of tubular profile shows hyperchromatic nuclei and mitotic figures. The total score for each kidney was calculated by addition of all 100 scores with a maximum score of 300.

Reverse-transcriptase Polymerase Chain Reaction (RT-PCR)

Total RNA was extracted with Trizol reagent (Invitrogen Corporation, Carlsbad, Calif.) from total kidney. For first strand cDNA synthesis, 1.5 µg of total RNA was used in a single-round RT-reaction. The reaction mixture consisted of 0.9 µL Oligo (dT)12-18 primer, 1.0 mM dNTPs, 1× first strand buffer, 0.4 mM DTT, 80 units RNaseout recombinant ribonuclease inhibitor, and 300 units of superscript II RNase H (Invitrogen Corporation, Carlsbad, Calif.). PCR was run by using 1 µL of the RT reaction mixture as the template, 0.4 µM of gene specific primers, 1×PC2 buffer, 0.25 mMdNTPs, and 1.5 units of KlenTaq DNA polymerase (Ab Peptides Inc., St. Louis, Mo.). The amplification was carried out at 94° C. for 2 min, then for 25 cycles at 94° C. for 30 sec, 58° C. for 45 sec, and 72° C. for 30 sec, followed by a final extension at 72° C. for 10 min. The primers were list in table. 1. β-actin and each target gene product were electrophoretically-separated on a 1% agarose gel and stained with ethidium bromide.

Real-time PCR was performed on an ABI Prism 7700 Sequence Detection System (Applied Biosystems, Foster City, Calif., USA). All of the probes and primers were Assays-on-Demand Gene expression products (Applied Biosystems). Real-time PCR reactions were using 10 µl of cDNA, 12.5 µl of TaqMan Universal PCR Master Mix (Applied Biosystems), 1.25 µl of the specific probe/primer mixed in a total volume of 25 µl. The thermal cycler conditions were as follows: 1×2 min 50° C., 1×10 min 95° C., 40 cycles denaturation (15 sec, 95° C.) and combined annealing/extension (1 min, 60° C.). Amplifications were normalized to β-actin using 2-CT method (Applied Biosystems).

Western Blot Analysis

Each sample was run on a 12% SDS-PAGE gel. The gel was electro-blotted onto a nitrocellulose membrane, incubated for 1 h in 20 ml of blocking buffer (TBS, 5% skim milk), washed three times in TEST, and incubated with goat anti-S100a6, goat anti-Anxa2, rabbit anti-PCNA antibodies (Santa Cruz Biotechnology Inc., Santa Cruz, Calif.) at 4° C. overnight. Blots were washed three times and incubated horseradish peroxidase-conjugated rabbit anti-goat or goat anti-rabbit antibodies (Pierce, Ill., USA) for 1 h at room temperature. Membranes were washed three times, and the membranebound antibody detected was incubated chemiluminescent reagent plus (PerinElmer Life Sciences, MA, USA) and captured on x-ray film.

Immunohistochemical Staining

Immunohistochemical staining was performed on formaldehyde-fixed and paraffin-embedded tissues using the avidin-biotin immunoperoxidase method [15]. The antibodies used included goat anti-annexin A2, goat anti-S100A6, rabbit anti-PCNA (Santa Cruz Biotechnology Inc., Santa Cruz, Calif.) and goat anti-vimentin (ICN Biomedicals Inc., Irvine, Calif.). Paraffin was removed from sections and followed by rehydration. Endogenous peroxidase activity was quenched and the sections were blocked with 1% w/v BSA in PBS for 1 hour. The sections were then incubated with a 1:100 dilution of goat polyclonal anti-S100A6 antibody in PBS. After incubation with a biotinylated secondary antibody (DAKO, Glostrup, Denmark), the tissue sections were treated with an avidin-biotin-peroxidase complex (DAKO, Glostrup, Denmark). The reaction was visualized by use of a 3,3'-diaminobenzidine chromogen (DAKO, Glostrup, Denmark) following tissue counterstaining with hematoxylin. For double staining, the slides were incubated with the first antibody, which was demonstrated by the ABC method described above and microwaved with citrate buffer. Subsequently, the slides were incubated with the second antibody for 1 h, which was visualized by an alkaline phosphatase mediated reaction as described previously [16]. Quantitative analysis for S100A6, annexin A2, and PCNA was performed at high power (200×) by optical microscopy. Twenty randomly selected cortical fields were examined in each section. Preliminary examinations established that the renal tubules were the major portion that was positively stained.

A proportion score and intensity score were assigned. The proportion score represented the estimated the percentages of positive tubular cells (1=0-20%, 2=20-40%, 3=40-60%, 4=60-80% and 5=80-100%). The intensity score represented the estimated average staining intensity of tubular cells (0=none, 1=weak, 2=intermediate, 3=strong). The overall amount of positive staining was then expressed as the sum of the proportion and intensity scores.

Immunoelectron Microscopic (IEM) Study

Samples were fixed in a mixture of 4% paraformaldehyde and 0.5% glutaraldehyde in PBS, pH 7.4 and prepared routinely for electron microscopy with final embedding in LR White resin as described previously [15]. Ultra-thin sections were cut and placed on nickel grids. Primary (goat anti-annexin A2; 1:100; Santa Cruz, Calif.) and secondary antibodies (1:40; gold labeled, British Biocell International, Cardiff, UK) were applied. The presence and localization of the 10 nm gold particles were examined under an electron microscope.

In Situ Hybridization

In brief, 3 μm paraffin sections were mounted on charged glass slides and stored in airtight boxes at 70° C. Riboprobes were generated by using a pGEMT-EASY plasmid containing cDNA insert of mouse annexin A2 and S100A6 to generate antisense transcripts for in situ hybridization. In vitro transcription was carried out using a commercial kit. For in situ hybridization, Dig-labeled mRNAs were diluted 100-fold in hybridization buffer containing 2 mMEDTA (pH 7.5), 20 mMTris (pH 7.5), 0.6 M NaCl, 2×Denhardt's solution, 20% dextran sulfate, 0.1 mg/ml tRNA, and 0.2 M dithiothreitol. After deparaffinization, kidney sections were digested with 20 μg/ml proteinase K in PBS for 20 mins. Sections were acetylated using 0.25% acetic anhydride in 0.1M triethanolamine for 10 min. A volume of 25-50 μl of hybridization mixture was placed on each section and covered with a siliconized glass coverslips.

Hybridization was performed in moist chambers at 42° C. for 16 h. Coverslips were removed by washing in 1× saline sodium citrate (SSC) at room temperature and 0.2×SSC for 10 min at room temperature. Slides were then washed in 0.05×SSC for 10 min at room temperature followed by a washing step in 0.025×SSC for 30 min at 37° C.

After rinsing the slides in maleic buffer (0.1M maleic acid, pH 7.5; 0.15M NaCl) for 1 min at room temperature and blocking with 1× blocking buffer 60 mins then incubated with riboprobes (1:200) at 42° C. over night. Wash with maleic buffer and develop with NBT/BCIP solution in dark. With double staining, slides were microwaved with citrate buffer and treated for IHC as reported previously in this article.

Statistical Analysis

All results were expressed as means±standard deviations. Comparisons between two groups were made by unpaired Student's t-test. Differences among multiple groups were determined with the one-way ANOVA using Tukey's method for post-hoc analysis. P<0.05 was considered statistically different.

Example 1

Detecting ATN with Biomarkers in the Present Invention

In uranyl-nitrate induced ATN animal model, creatinine and BUN (Blood Urea Nitrogen) are measured in different time course. The result are shown in FIG. 1. In mice that received a single dose of uranyl nitrate, the levels of serum creatinine (Cr) rapidly increased to reach 1.554±0.371 mg/dL by day 3, as compared to normal controls (0.13±0.03 mg/dL) (FIG. 1a). This difference was significant (p<0.05). Thereafter, Cr levels gradually declined. By day 14 following uranyl nitrate injection, the Cr levels (0.29±0.19 mg/dL) approached control values (FIG. 1a). A similar trend and significance (FIG. 1b) was observed for serum BUN 127.85±11.76 mg/dL on day 3 and 26.53±8.76 mg/dL on day 14, compared to 24.58±1.78 mg/dL in normal controls, p<0.05.

Figure 2:
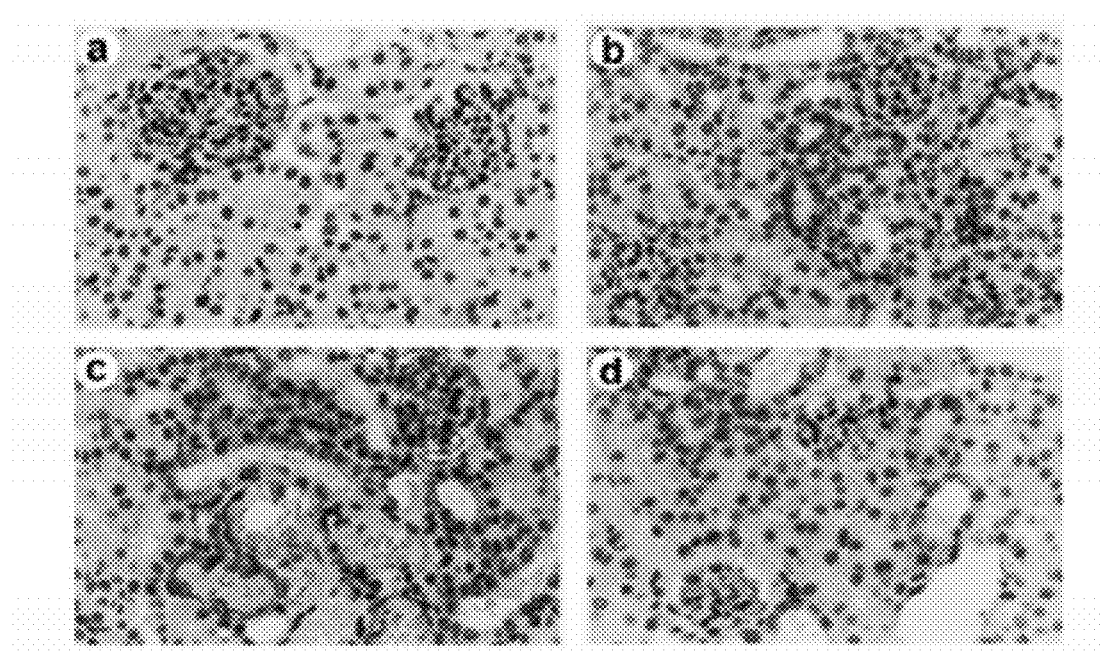
FIG. 2a-d shows immunohistochemical staining of renal section in uranyl-nitrate induced ATN animal mode of the example 1. A dedifferentiation marker-anti-vimentin antibody is used.

Microscopic examination of renal tissue sections from the mice that received uranyl nitrate showed focal necrosis of renal tubules 3 days after injection (FIG. 1d, g), followed by a more diffuse and intense pattern on day 7 (FIG. 1e, g). Regeneration of renal tubules was noted on day 7 (FIG. 1h). On day 14 the histological alterations were mild and had been mostly replaced by regenerating tubules (FIG. 1f, h) and a normal background (FIG. 1a). Immunohistochemical staining of renal section with anti-vimentin, a cellular dedifferentiation marker, showed the proximal tubular cells undergo cell dedifferentiation to re-enter the cell cycle during the 14 days of disease progression. In normal kidney cells, vimentin expression was restricted to podocytes of glomeruli and fibroblasts in the interstitium (FIG. 2a). However, the regenerating tubular cells of the ATN mouse model strongly expressed the vimentin protein on day 7 (FIG. 2c). A gradual decline in the protein level occurred thereafter and then declined gradually on day 14 (FIG. 2d).

Figure 3:
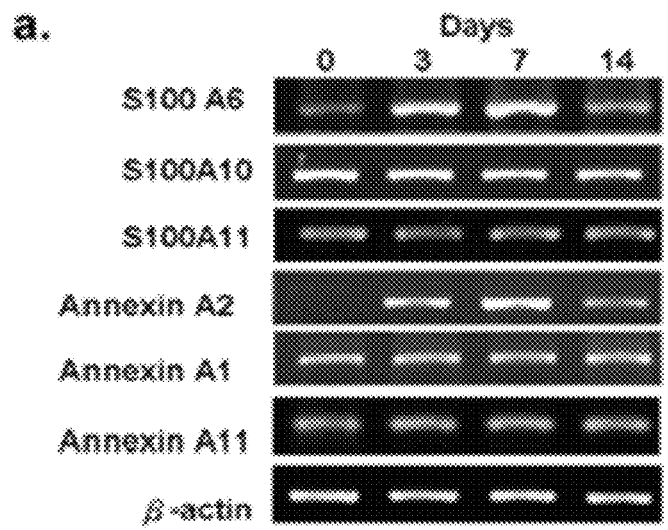
FIG. 3a shows gene expression of S100A6, S100A10, S100A11, annexin A1, and annexin A2 with RT-PCR in the example 1.
FIG. 3b shows relative fold change of S100A6 in uranyl-nitrate induced ATN animal model of the example 1.
FIG. 3c shows relative fold change of annexin A2 in uranyl-nitrate induced ATN animal model of the example 1.
Figure 3:
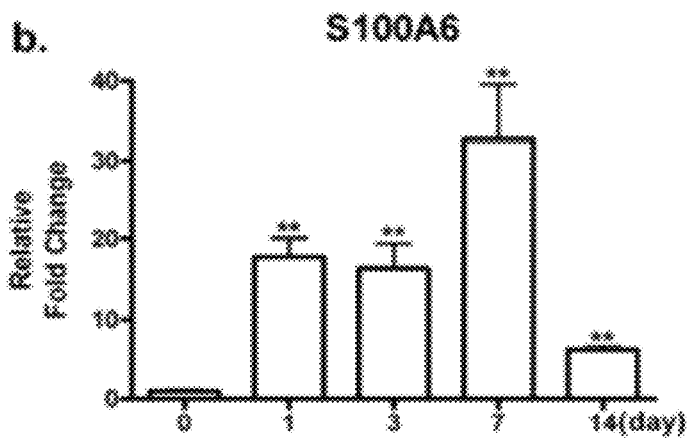
Figure 3:
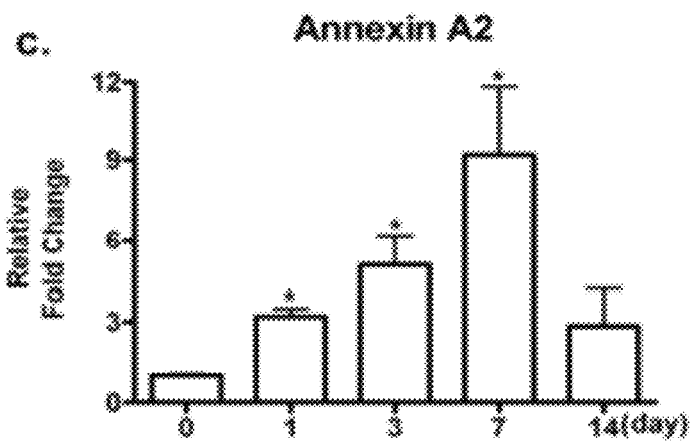

The expression of genes encoding S100A6, S100A10, S100A11, annexin A2, annexin A1, and annexin A11 was examined by using regular RT-PCR followed by quantification by real-time RT-PCR. As shown in FIG. 3, there was an increase of S100A6 and annexin A2 in the progressive of uranyl-nitrate induced ATN. In contrast, there was no significant change in the expression of S100A10, S100A11, annexin A1 and annexin A11. These results indicate that during the period of dedifferentiation and regeneration in uranyl nitrate-induced ATN, the $Ca^{2+}$-binding proteins S100A6 and annexin A2 are selectively associated with the induction and recovery process.

To examine the cellular distribution and association of S100A6 and annexin A2 with ARF, immunohistochemical staining was performed. Paraffin-embedded renal sections from control and from uranyl nitrate induced-mice kidneys were harvested at timed intervals (0, 3, 7 and 14 days) after induction. The expression of S100A6 and annexin A2 results indicated that in the kidneys of control animals (day 0), the S100A6 (FIG. 4a) and annexin A2 (FIG. 4b) are expressed in a very limited number of renal tubular epithelial cells (<0.10). However, the expression of S100A6 and annexin A2 increased significantly at 7 day after induction. At this time point, both the number of the renal tubular epithelial cells expressing S100A6 (FIG. 4e) and annexin A2 (FIG. 4f) and the intensity of their staining increased significantly. Expression of S100A6 (FIG. 4c) and annexin A2 (FIG. 4d) at day 3 was greater than that of the control but considerably less than that at day 7. S100A6 and annexin A2 staining in kidney sections after day 7 indicates considerable variation, with some tubules demonstrating no labeling in any cell, whereas in some tubules all cells expressed S100A6 and annexin A2. The results indicate that S100A6 and annexin A2-positive cells are primarily located in the inner cortical and outer medullary regions (corticomedullary junction) of the kidney, a region that contains the S3 segment of the proximal tubules.

Figure 4:
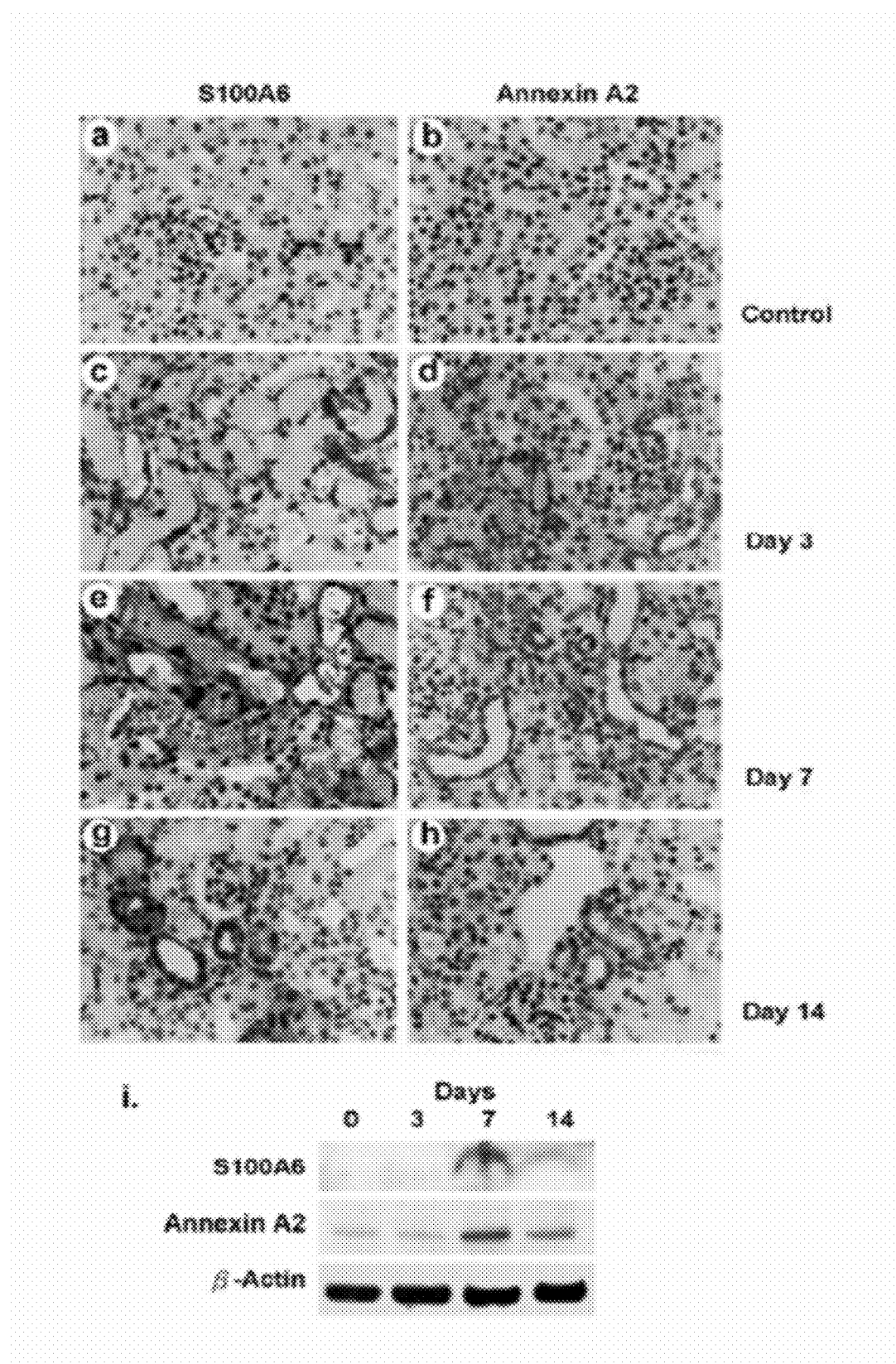
FIG. 4a-h shows expression and renal distribution of S100A6 protein and annexin A2 protein with immunofluorescence staining of S100A6 protein and annexin A2 protein in uranyl-nitrate induced ATN animal model of the example 1.
FIG. 4i shows expression amount of S100A6 protein and annexin A2 protein with Western-blot in uranyl-nitrate induced ATN animal model of the example 1.

Similarly, the expression of annexin A2 protein in the kidney showed the same pattern as that of the S100A6, with the intensity of protein staining being less than the S100A6 by Western blot analysis (FIG. 4i). Besides, the expression pattern of these proteins in the kidney sections was similar to that of vimentin during the recovery phase.

Figure 5:
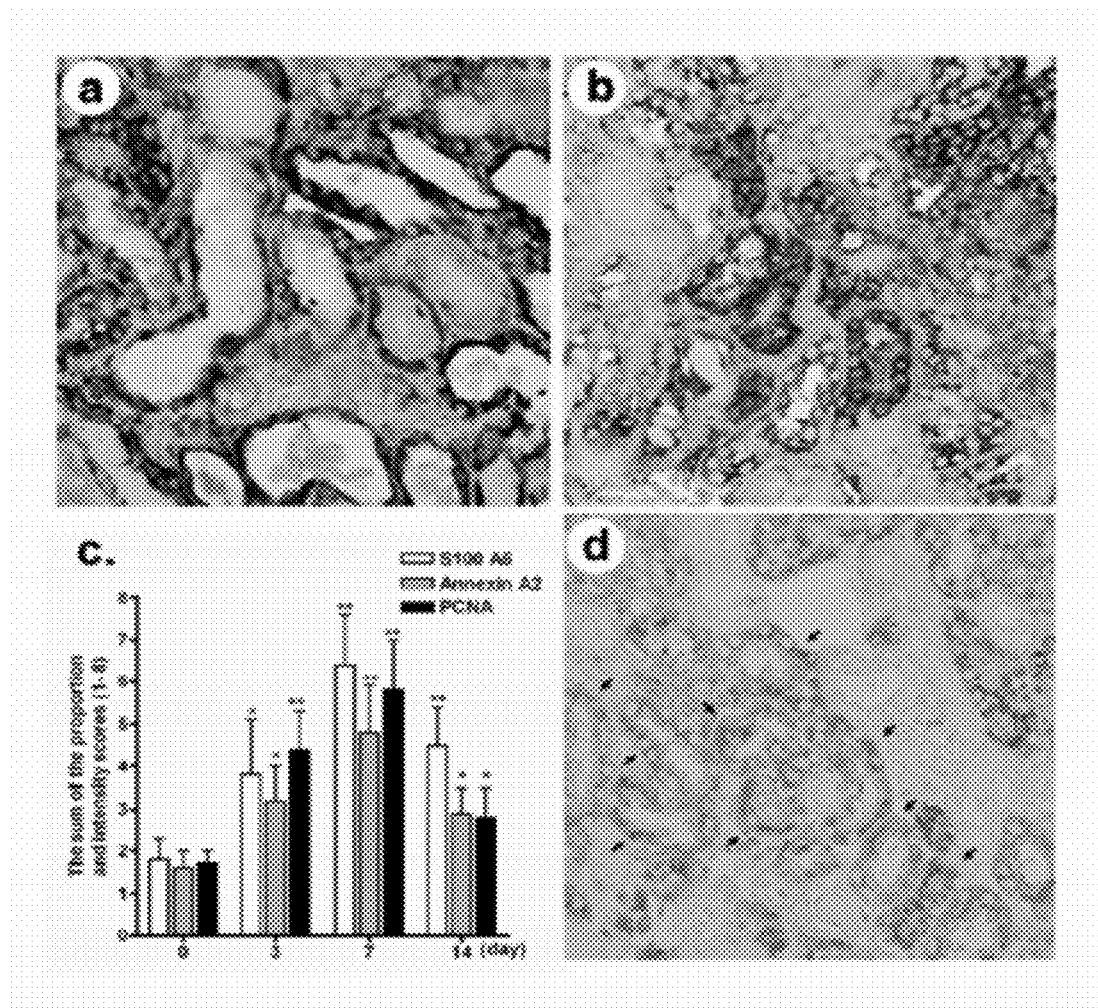
FIG. 5 shows proliferation morphology of renal tube and the co-expression of S100A6 protein and annexin A2 protein with in-situ hybridization in uranyl-nitrate induced ATN animal model of the example 1.

ATN involves both the loss of epithelial cell polarity and the onset of proliferative response. Therefore, to determine the relevance of the S100A6 and annexin A2 to these processes, we examined the proliferative status of renal tubular epithelial cells and co-expression of these two proteins. Kidney sections, obtained on day 7 after uranyl nitrate treatment, were double stained with ribo-probes against both S100A6 and annexin A2 mRNA and with the antibody against PCNA, a marker of cell proliferation. The majority of cells (>80%) expressing S100A6 (dark blue color—FIG. 5a) and annexin A2 (dark blue color—FIG. 5b) and were also PCNA positive (red color—FIG. 5).

Semi-quantitative scoring analysis revealed concordant patterns of abundance among the three proteins (FIG. 5c). Besides, co-localization of both S100A6 and annexin A2 was evaluated by double staining. Most of the regenerating tubular cells were found to express the proteins simultaneously (FIG. 5d).

Example 2

Detecting ATN with Biomarkers in the Present Invention

Figure 6:
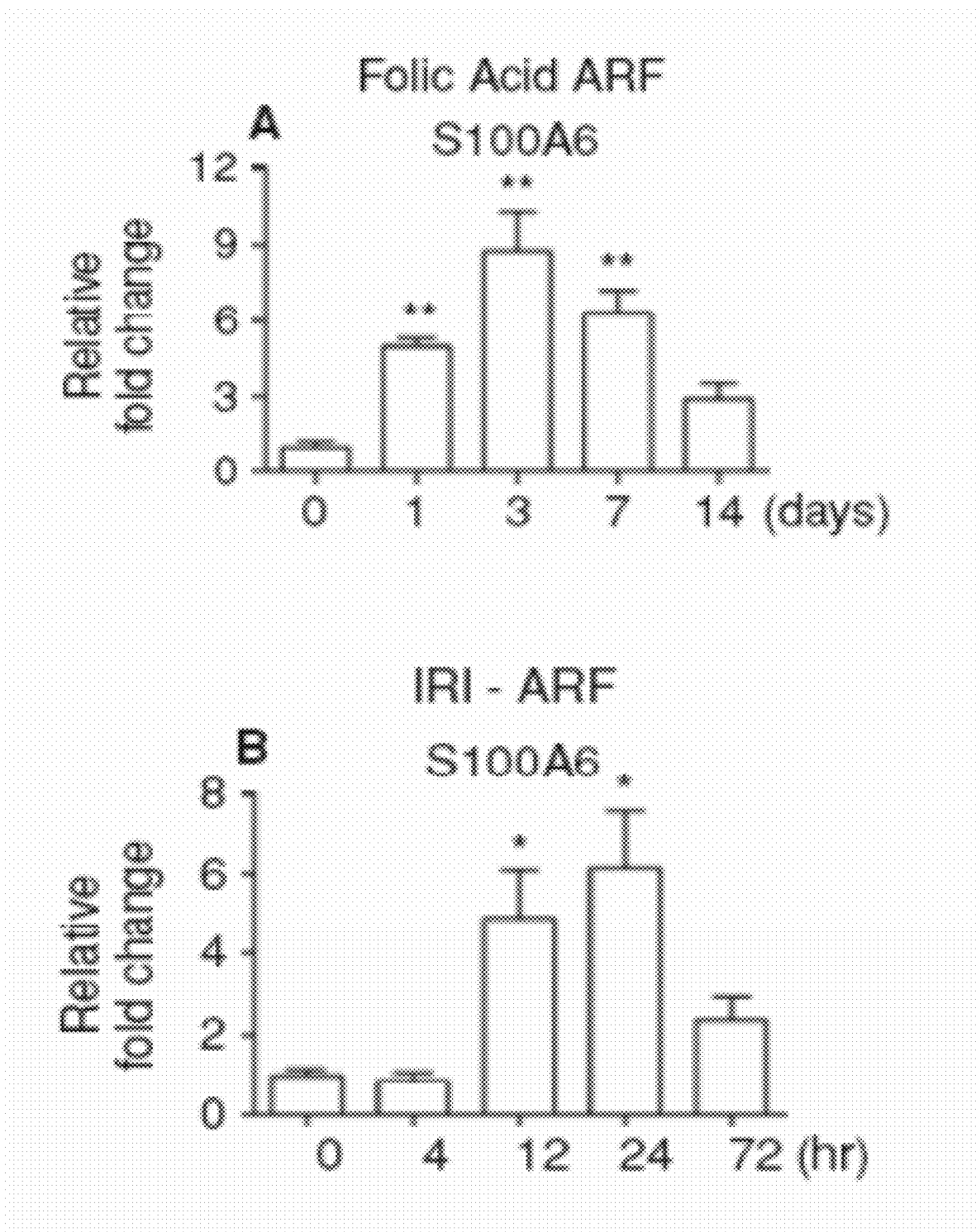
FIG. 6 shows expression and renal distribution of S100A6 protein and annexin A2 protein in the nephrotoxin model of folic acid induced ATN and rapid acute renal failure model of ischemia-reperfusion injury (IRI).
Figure 6:
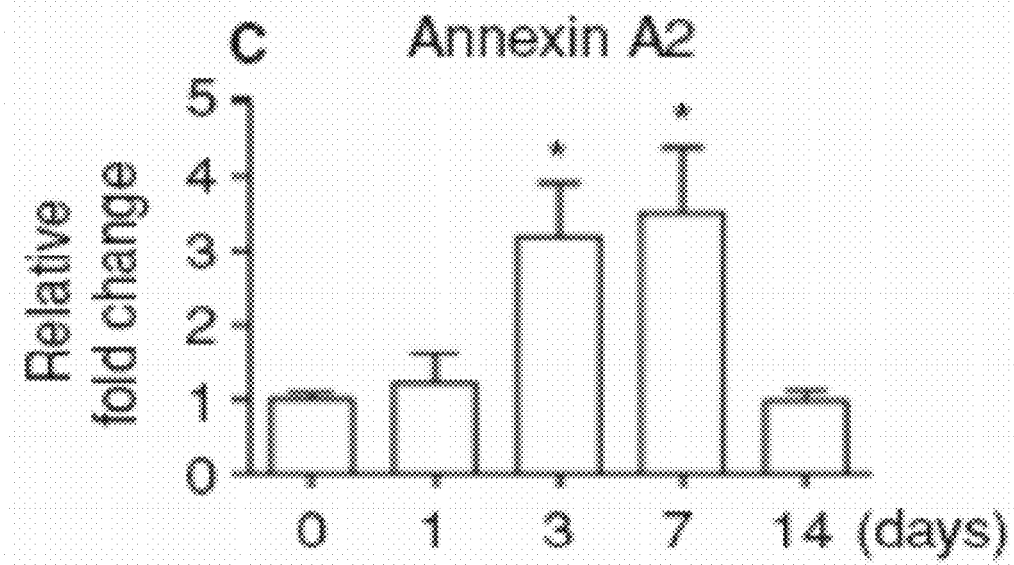
Figure 6:
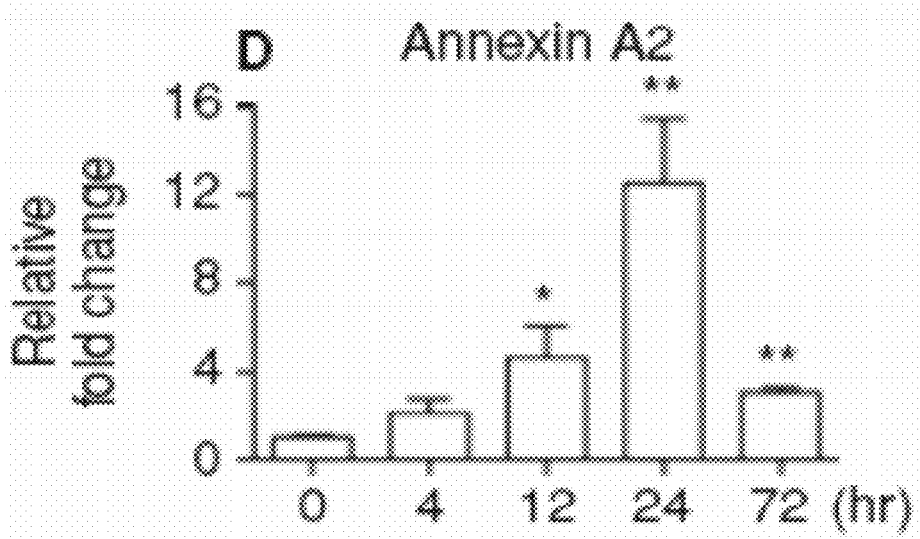

To determine the general relevance of S100A6 and annexin A2 expression to the pathophysiology of acute renal failure, we examined their expression in two different mouse models. In the nephrotoxin model of folic acid induced acute renal failure, the temporal pattern of S100A6 and annexin A2 expression (FIG. 6a, c) was reminiscent of uranyl nitrate model that peaked between day 3 and 7 and returned to normal level by day 14. The expression of PCNA also peaked between day 3 and day 7. More importantly, in the rapid acute renal failure model of ischemia-reperfusion injury, the expression of S100A6 and annexin A2 (FIG. 6b, d) were elevated early (12 hours) and declined to normal level (72 hours) as a respective sensor of tubular injury and recovery.

During the course of our studies on global gene expression profiling in a mouse model of uranyl nitrate-induced acute renal failure, we observed dramatic up-regulation in the expression of S100A6 (calcyclin) and annexin A2. Accordingly, we postulated these interactive effector molecules might play a role in the pathophysiology of acute renal failure and their expression might be useful biomarkers of the temporal events and processes of the tubular epithelial cell in ATN.

In summary, oligonucleotide sequence and/or amino acid sequence of annexin A2 and/or S100A6 in the present invention are effective biomarkers for detecting ATN-related ARF and deserved to be applied in clinical acute renal failure diagnosis.

OTHER EMBODIMENTS

All features disclosed herein may be combined in any form with other methods and replaced by other features with identical, equivalent or similar purpose. Thus except for the part that is specifically emphasized, all features disclosed herein constitute only one embodiment among the numerous equivalent or similar features.

All modifications and alterations to the descriptions disclosed herein made by those skilled in the art without departing from the spirits of the invention and appended claims shall remain within the protected scope and claims of the invention.

REFERENCES

1. Lieberthal W, Koh J S, Levine J S: Necrosis and apoptosis in acute renal failure. *Semin Nephrol* 18:505-518, 1998
2. Lim I K, Lee K H, Han B D, et al.: Uranyl nitrate induced polyuric acute tubular necrosis in rats. *Yonsei Med J* 28:38-48, 1987
3. Lieberthal W. Nigam S K: Acute renal failure. II. Experimental models of acute renal failure: imperfect but indispensable. *Am J Physiol Renal Physiol* 278:F1-F12, 2000
4. Bulger R E: Renal damage caused by heavy metals. *Toxicol Pathol* 14:58-65, 1986
5. Toback F G: Regeneration after acute tubular necrosis. *Kidney Int* 41:226-246, 1992
6. Nigam S. Lieberthal W: Acute renal failure. III. The role of growth factors in the process of renal regeneration and repair. *Am J Physiol Renal Physiol* 279:F3-F1.1, 2000
7. Heimann C W: Calcium-binding proteins: basic concepts and clinical implications. *Gen Physiol Biophys* 11:411-425, 1992
8. Raynal P. Pollard H B: Annexins: the problem of assessing the biological role for a gene family of multifunctional calcium- and phospholipid-binding proteins. *Biochim Biophys Acta* 1197:63-93, 1994
9. Morgan R O, Fernandez M P: Annexin gene structures and molecular evolutionary genetics. *Cell Mol Life Sci* 53:508-515, 1997
10. Donato R: Intracellular and extracellular roles of S100 proteins. *Microsc Res. Tech* 60:540-551, 2003
11. Mishra J, Ma Q, Prada A, et al.: Identification of neutrophil gelatinase-associated lipocalin as a novel early urinary biomarker for ischemic renal injury. *J Am Soc Nephrol* 14:2534-2543, 2003
12. Long D A, Woolf A S, Suda T, et al.: Increased renal angiopoietin-1 expression in folic acid-induced nephrotoxicity in mice. *J. Am Soc Nephrol* 12:2721-2731, 2001
13. Chen A, Sheu L F, Ho Y S, et al.: Experimental focal segmental glomerulosclerosis in mice. *Nephron* 78:440-452, 1998
14. Kumar V Abbas A K. Fausto N: Robbins & Cotran Pathologic Basis of Disease, 7th edition. 994-995, 2005
15. Chen A, Chou W Y, Ding. S L, at al.: Glomerular localization of nephritogenic protein complexes on a nonimmunologic basis. *Lab Invest* 67:175-185±1992
16. Ricotta J M, Xu Y C, Arar M, at al.: Morphological insights into the origin of glomerular endothelial and mesangial cells and their precursors. *J Histochem Cytochem* 51:141-150, 2003

What is claimed is:

1. A method for diagnosing a kidney disease in a subject, comprising
   providing a renal sample obtained from a subject, wherein the renal sample is a renal cortical tissue,
   detecting in the renal sample a level of a biomarker, which is Annexin A2, and
   determining, based on the level of the biomarker thus detected, whether the subject suffers from a kidney disease, which is acute kidney failure or acute tubular necrosis; wherein an elevated level of the biomarker in the subject relative to that in a healthy subject indicates that the subject suffers from the kidney disease.

2. The method of claim 1, wherein the detecting step is performed by examining the protein level of Annexin A2.

3. The method of claim 2, wherein the protein level of Annexin A2 is determined by an immune assay selected from the group consisting of ELISA, Western Blot, and immunohistochemical staining.

4. The method of claim 3, wherein the immune assay is ELISA.

5. The method of claim 3, wherein the immune assay is Western Blot.

6. The method of claim 3, wherein the immune assay is immunohistochemical staining.

7. The method of claim 1, wherein the detecting step is performed by examining the messenger RNA level of Annexin A2.

8. The method of claim 7, wherein the RNA level of Annexin A2 is determined by real-time PCR.

9. The method of claim 7, wherein the RNA level of Annexin A2 is determined by in situ hybridization.

* * * * *